United States Patent [19]
Shao et al.

[11] Patent Number: 5,620,883
[45] Date of Patent: Apr. 15, 1997

[54] LIVING CELLS MICROENCAPSULATED IN A POLYMERIC MEMBRANE HAVING TWO LAYERS

[75] Inventors: Wen Shao, Baltimore; Kam W. Leong, Ellicott City, both of Md.

[73] Assignee: The Johns Hopkins University, Baltimore, Md.

[21] Appl. No.: 221,627

[22] Filed: Apr. 1, 1994

[51] Int. Cl.$^6$ .......................... C12N 11/00; C12N 11/02; C12N 11/10

[52] U.S. Cl. .................. 435/174; 264/4.32; 424/93.1; 424/408; 424/459; 424/460; 424/462; 424/491; 424/497; 435/177; 435/178; 435/182; 514/963; 514/970

[58] Field of Search .................. 435/174, 177, 435/178, 182; 264/4.32; 424/93 R, 408, 459, 460, 462, 491, 497, 93.1; 514/963, 970

[56] References Cited

U.S. PATENT DOCUMENTS

| | | | |
|---|---|---|---|
| 3,714,065 | 1/1973 | Kitajima et al. | 252/316 |
| 4,349,530 | 9/1982 | Royer | 424/19 |
| 4,352,883 | 10/1982 | Lim | 435/178 |
| 4,749,620 | 6/1988 | Rha et al. | 428/402.2 |
| 4,798,786 | 1/1989 | Tice et al. | 435/177 |
| 4,861,627 | 8/1989 | Mathiowitz et al. | 427/213.31 |
| 4,942,129 | 7/1990 | Goosen et al. | 435/182 |

FOREIGN PATENT DOCUMENTS

WO91/10425  7/1991  WIPO.

OTHER PUBLICATIONS

Aebischer, P., et al., Transplantation of Polymer Encapsulated Neurotransmitter Secreting Cells: Effect of the Encapsulation Technique, Transaction of the ASME, 1991, 113:178–183.

Chang, T.M.S., *Artificial Cells*, 1972, Springfield, IL: Charles C. Thomas, pp. 9–10.

Aebischer, P., et al., Macroencapsulation of dopamine-secreting cells by coextrusion with an organic polymer solution, Biomaterials, 1991, 12:50–56.

Aebischer, p., et al., Transplantation of microencapsulated bovine chromaffin cells reduces lesion–induced rotational asymmetry in rats, Brain Res., 1991. 560(1–2):43–49.

Babensee, J.E., et al., Morphological assessment of hepatoma cells (HepG2) microencapsulated in a HEMA–MMA copolymer with and without Matrigel, J. Biomed. Matr. Res., 1992, 26:1401–1418.

Becker J., et al. Sustained behavioral recovery from unilateral nigrostriatal damage produced by the controlled release of dopamine from a silicone polymer pellet placed into the denervated striatum, Brain Res., 1990, 508:60–64.

Behara, A.M., et al., Intrathymic implants of genetically modified fibroblasts, FASEB J., 1992, 6:2853–2858.

Boag, et al., Microencapsulation of human fibroblasts in a water–insoluble polyacrylate, Biotech. Bioeng., 1987, 30:954–962.

Broughton, et al., Effect of capsule permeability on growth of CHO cells in Eudragit RL microcapsules: Use of FITC–dextran as a marker of capsule quality, Biomaterials, 1989.30:462–465.

Cadic, et al., "Inverted Microcarriers" for cell cultures made by polymerization of shells around agarose microspheres in a non–cytotoxic procedure, Polymer, 1991, 23(8):933–937.

Cai, et al., Development and evaluation of a system of microencapsulation of primary rat hepatocytes, Hepatology, 1989, 10:855–860.

Calafiore, Transplantation of microencapsulated pancreatic human islets for therapy of diabetes mellitus, ASAIO J., 1992, 32:34–37.

Crooks, et al., Microencapsulation of mammalian cells in a HEMA–MMA copolymer: Effects on capsule morphology and permeability, J. Biomed. Matr. Res., 1990, 24:1241–1262.

(List continued on next page.)

*Primary Examiner*—David M. Naff
*Assistant Examiner*—Deborah Ware
*Attorney, Agent, or Firm*—Banner & Witcoff, Ltd.

[57] ABSTRACT

A biocompatible microcapsule containing living cells encapsulated in a membrane is disclosed. The membrane is a complex formed by the cohesion of two polymer layers. An inner layer comprises a substrate biopolymer and an outer layer comprises a synthetic polyelectrolyte having an electrolytic charge opposite that of the substrate biopolymer. Droplets of a solution of substrate biopolymer containing a suspension of living cells can be added to a solution comprising the synthetic polyelectrolyte to form the encapsulates. The membrane is formed by the cohesion of the oppositely-charge polymer layers to form a complex of substrate biopolymer and synthetic polyelectrolyte. Preferably, the inner layer contains a cationic biopolymer, such as collagen modified to have a pKI of 9, or an anionic biopolymer such as esterified or modified hyaluronic acid. Further, the membrane is permeable to materials which are able to maintain normal metabolic functions of bioactive cells which are encapsulated in the inner layer of the membrane. In addition the membrane is permeable to products released by the bioactive cells and impermeable to agents of the immune system which are responsible for immunological reactions that result in an immune rejection of bioactive cells and products thereof.

5 Claims, No Drawings

OTHER PUBLICATIONS

Dahiyat, et al., Synthesis and characterization of putrescine based poly(phosphoester–urethanes), J. Biomat. Sci., 1993, 4:529–543.

Doering, Expression of a novel gene product by transplants of genetically modified primary fibroblasts in the central nervous system, J. NeuroSci. Res., 1991, 29(3):292–298.

Goosen, et al., Optimization of microencapsulation parameters: Semipermeable microcapsules as a bioartifical pancreas, Biotech. Bioeng., 1985, 27:146–150.

Lacy, et al., Maintenance of normoglycemia in diabetic mice by subcutaneous xenografts of encapsulated islets, Science, 1991, 254:1782–1784.

Lim, et al., Microencapsulated islets as bioartificial endocrine pancreas, Science, 1980, 210:908–910.

Mallabone, et al., Microencapsulation of a human diploid fibroblasts in cationic polyacrylates, Biomaterials, 1989, 10:380–386.

Sagen, Chromaffin cell transplants for alleviation of chronic pain, ASAIO J., 1992, 38:24–28.

Shao, et al., Microcapsules through polymer complexation I: Complex coacervation of polymers containing a high charge density, Biomaterials, 1991, 12;374–384.

Shao, et al., Microcapsules through hpolymer complexation II: By complex coacervation of polymers containing a low charge density, Biomaterials, 1991, 12:479–488.

Sun, et al., In vitro and in vivo evaluation of microencapsulated porcine islets, ASAIO J., 1992, 38:125–127.

Tresco, et al., Polymer encapsulated neurotransmitter secreting cells, ASAIO J., 1992, 38:17–23.

Wong, et al., Microencapsulation of cells within alginate poly–l–lysine microcapsules prepared with standard single step drop technique histologically identified membrane imperfections and the associated graft rejections, J. Biomat. Artificial Cells Immob. Biotech., 1991, 19:675–685.

Wong, et al., A novel two–step procedure for immobilizing living cells in microcapsules for improving xenograft survival, J. Biomat. Artificial Cells Immob. Biotech., 1991, 19:687–697.

5,620,883

LIVING CELLS MICROENCAPSULATED IN A POLYMERIC MEMBRANE HAVING TWO LAYERS

BACKGROUND OF THE INVENTION

1. Field of the Invention

This invention relates to living cells encapsulated in a polymeric membrane. More particularly, this invention relates to living cells encapsulated in a cohesive permselective membrane comprising a biopolymer and a polyelectrolyte.

2. Description of Related Art

The use of microencapsulated cells as hybrid artificial organs was first proposed in 1964. Endocrine cells, islets, and hepatocytes were proposed to be encapsulated by micropheres formed by the complexation between alginate and calcium. [Chang, T. M. S., *Artificial Cells*, 1972, Springfield, Ill. Charles C. Thomas.] Intensive studies of these artificial cells, however, began only in the last decade; earlier studies failed to produce semipermeable microcapsules that have the right permeability and soft tissue biocompatibility. In the 1980's, islets of Langerhans were encapsulated in alginate-poly-l-lysine-alginate capsules. [Lim, F. and A. M. Sun, *Microencapsulated islets as bioartificial endocrine pancreas*. Science, 1980. 210: p. 908.] By using purer alginate and more viscous alginate solutions, researcher obtained microcapsules that were impermeable to normal serum immunoglobulin. [Goosen, M. F. A., et al., *Optimization of microencapsulation parameters: Semipermeable microcapsules as a bioartificial pancreas*. Biotech. Bioeng., 1985.27: p. 146.] Implantation in the intraperitoneal space of diabetic rats also reversed the diabetic state of some animals for up to one year.

Continued refinement of the system led to restoration of normoglycemia by microencapsulated porcine islets in 13 to 18 mice for up to ten months [Sun, A. M., et al., *In vitro and in vivo evaluation of microencapsulated porcine islets*. ASAIO J, 1992. 38: p. 125.] Individually encapsulated rat islets placed in the intercapillary space of hollow fibers made of poly(acrylonitrile-co-vinyl chloride) were implanted into diabetic rats. [Lacy, P. E., et al., *Maintenance of normoglycemia in diabetic mice by subcutaneous xenografts of encapsulated islets*. Science, 1991. 254: p. 1782.] Over 80 percent of the animals maintained normoglycemia for at least 60 days. These systems remain promising as a clinical treatment for diabetes mellitus. [Calafiore, R., Transplantation of *microencapsulated pancreatic human islets for therapy of diabetes mellitus*. ASAIO J, 1992.38: p. 34.]

Another promising use of these microencapsulation systems is in construction of hybrid artificial liver. Current therapy for fulminant hepatic failure is plagued by severe donor shortage and complications associated with liver transplantation. Hepatocyte transplantation represents an attractive alternative. The major hurdle is immunological rejection, which potentially can be resolved by microencapsulation. Even in a hollow fiber configuration, microencapsulation might still be necessary and advantageous over free hepatocytes because aggregated hepatocytes might remain viable and functional for a longer period of time.

Rat hepatocytes encapsulated by the above-described alginate-polylysine system has been shown in vitro to maintain part of the functions for up to five weeks. [Cai, Z., et al., *Development and evaluation of a system of microencapsulation of primary rat hepatocytes*. Hepatology, 1989. 10: p. 855.] In this case, however, the nature of the substrate may be more crucial than the case for artificial pancreas. Hepatocyte does not proliferate in culture and loses many of its differentiated functions rapidly. The alginate-polylysine substrate appears to be inferior to collagen-coated substrate in maintaining those term functions, and that remains to be the greatest challenge.

Pertinent to the goals of rehabilitation engineering is implantation of polymer encapsulated neurotransmitter secreting cells for various central nervous system (CNS) deficits. This is an attractive idea since drug delivery to the brain is always plagued by low bioavailability caused by the presence of the blood-brain-barrier (BBB). Because only small or lipophilic agents can cross the BBB, potent biomacromolecules such as nerve growth factors cannot be effectively delivered by conventional means. In response to dopamine deficiency associated with Parkinson's disease, local drug delivery systems such as pumps or controlled release polymers have been implanted intracranially to remedy the deficit. [Becker, J., et al., *Sustained behavioral recovery from unilateral nigrostriatal damage produced by the controlled release of dopamine from a silicone polymer pellet placed into the denervated striatum*. Brain Res., 1990. 508: p. 60.] While improved function has been reported in various experimental animal models, there are problems of dopamine autoxidation and cavitation around the injection site. As frequent replacements of devices in the brain is highly impractical, the limited service life-time of controlled release systems also renders this approach less attractive.

Transplantation of dopaminergic tissues into the striatum represents a potential solution. Nevertheless, although the transplanted fetal neurons can survive and make synaptic contacts with the host striatal neurons, there are formidable hurdles to be overcome. They include failure to reestablish the normal neural circuitry, high mortality and morbidity associated with the transplant procedure, and the ethical issue of human fetal tissue research. [Aebischer, P., et al., *Transplantation of polymer encapsulated neurotransmitter secreting cells: Effect of the encapsulating technique*. Transactions of the ASME, 1991. 113: p. 178.] It is also believed that over time the transplanted tissue will be rejected even if allogeneic tissue is used. To circumvent some of these obstacles, bovine adrenal medullary chromaffin cells and PC 12 cells were encapsulated in alginate/polylysine microcapsules or poly(acrylonitrile vinyl chloride) hollow fibers. [Aebischer, P., et al., *Macroencapsulation of dopamine-secreting cells by co extrusion with an organic polymer solution*. Biomaterials, 1991.12: p. 50; Tresco, P. A., S. R. Winn, and P. Aebischer, *Polymer encapsulated neurotransmitter secreting cells*. ASAIO J, 1992.38: p. 17.] In vitro studies show that at least some of the cells survived the encapsulation procedure. Release of dopamine from both the microcapsules and macrocapsules was observed in response to a chemically-induced depolarization. Encapsulated PC12 cells also alleviated lesion-induced rotational asymmetry in rats for least four weeks. [Aebischer, P., et al., *Transplantation of microencapsulated bovine chromaffin cells reduces lesion-induced rotational asymmetry in rats*. Brain Res., 1991. 560(1–2): p. 43.] Immunoprotection was demonstrated when both types of microcapsules were implanted in an immunologically incompatible host. [Dahiyat, B., et al., *Synthesis and characterization of putrescine based poly-(phosphoesterurethanes)*. J. Biomat. Sci., 1993: p. in press; Tresco, P. A., S. R. Winn, and P. Aebischer, *Polymer encapsulated neurotransmitter secreting cells*. ASAIO J, 1992.38: p. 17.]

Pain management is one of the major challenges of rehabilitation medicine. Conventional pharmacological intervention always require escalating doses and repeat administration. A recently reported promising approach for chronic pain management was to transplant adrenal medullary chromaffin cells into the spinal subarachnoid space. [Sagen, J., *Chromaffin cell transplants for alleviation of chronic pain*. ASAIO J, 1992.38: p. 24.] In rats the transplanted cells survived for months and released high levels of opioid peptides and catecholamines. In behavioral studies in rats, the transplants reduced pain in an arthritis model and a peripheral neuropathy model. Subsequent limited clinical trials demonstrated that the patients received pain relief over a period of 4–10 months, and a concomitant decrease in narcotic intake. Increased levels of catecholamines and metencephalon in the spinal CSF samples of patients also were observed. Success of this clinical trial was relied on the availability of human adrenal glands and the administration of the immunosuppressive agent cyclosporine A for two weeks. It appears that microencapsulated cells can bolster immensely the appeals of this cell-based management of chronic, and perhaps intractable, pain.

Human gene therapy depends on insertion of a desired gene into autologous cells. The success rate is low because of the difficulty of transfecting primary human cells. An alternative strategy is to genetically engineer easily transfectable cell lines from a non-autologous source to secrete a desired gene product. This approach was demonstrated in the secretion of significant levels of human growth hormone for weeks from mouse fibroblasts implanted in rat thymus. [Behara, A. M., A. J. Westcott, and P. L. Chang, *Intrathymic implants of genetically modified fibroblasts*. FASEB J., 1992.6: p. 2853; Doering, L. C. and P. L. Chang, *Expression of a novel gene product by transplants of genetically modified primary fibroblasts in the central nervous system*. I. NeuroSci. Res., 1991. 29(3): p. 292.] However, the novel gene product provoked an intense antibody response from its host recipient. Enclosing allogeneic recombinant cells in microcapsules should become an exciting approach in delivery of novel gene products.

Cells can be encapsulated in hollow fibers or in microcapsules that are several hundred microns in size. The former has the advantage of higher mechanical stability and retrievability. Microcapsules on other hand have a higher surface to volume ratio for growth of anchorage-dependent cells and lower mass transfer resistance for nutrients supply and product secretion. To combine the strength of the two approaches, microencapsulated cells can further be macroencapsulated, for instance, in hollow fibers; choice of highly permeable hollow fibers would add little to the overall mass transfer resistance. In the case of artificial pancreas design, this has the added advantage of preventing the islets from losing their bioactivity caused by aggregation. [Lacy, P. E., et al., *Maintenance of normoglycemia in diabetic mice by subcutaneous xenografts of encapsulated islets*. Science, 1991. 254: p. 1782.]

Microcapsule formulation is a known technology used by the pharmaceutical industry to manufacture sustained release products. However, the necessity of avoiding any harsh conditions that might damage cell viability eliminates many available methods. The most commonly used techniques for cell encapsulation are complex coacervation and interfacial precipitation. Complex coacervation involves the electrostatic interaction of two oppositely charged polyelectrolytes. At the right matching charge density, the two polyions combine and migrate to form a colloid-rich or water-insoluble phase. The molecular weight and chain conformation parameters of the polyions may also play an important role in the complexation process. Interfacial precipitation relies simply on the solidification of a dissolved polymer upon contact with an aqueous phase.

In the area of cell encapsulation, gelation of alginates is the most extensively studied system. Alginate is a glycuranan extracted from brown seaweed algae. Calcium or other multivalent counterions chelates contiguous blocks of alpha-1,4-L-guluronan residues present in the polysaccharide. Cell encapsulation is achieved when alginate solution containing suspended living cells is dropped or extruded into a solution containing calcium ions. The microcapsules formed can further be coated by adsorption of polyions such as polylysine, which can be coated by alginate again. Many cell types, including islets, hepatocytes, PC I12 cells, chondrocytes, and fibroblasts, have been encapsulated by this method.

The standard single step drop technique has been rejected not to be reproducible [Wong, H. and T. M. S. Chang, *Microencapsulation of cells within alginate poly-l-lysine microcapsules prepared with standard single step drop technique histologically identified membrane imperfections and the associated graft rejections*. J. Biomar. Artificial Cells Immob. Biotech., 1991. 19: p. 675.] A variable number of cells become embedded in the membrane matrix and some are exposed to the surface of the microcapsules.

When implanted in mice, this led to an undesirable acute cell-mediated host response. Macrophages and lymphocytes were also observed to perforate the membrane and infiltrate the microcapsules. A two-step microencapsulation procedure was reported to circumvent this problem. In essence, the above cell-containing microsphere is encapsulated one more time to form larger calcium alginate gel microspheres. After the larger microspheres are coated by poly-1-lysine outside, the contents inside are liquified by titrate to remove calcium, resulting in free floating cells that are not embedded in the capsule membrane. [Wong, H. and T. M. S. Chang, *A novel two-step procedure for immobilizing living cells in microcapsules for improving xenograft survival*. J. Biomat. Artificial Cells Immob. Biotech., 1991. 19: p. 687.]

Macrocapsules composed of totally synthetic polyelectrolytes were prepared by the complex coacervation principle. Polymers containing methacrylic acid (MAA) and dimethylaminoethyl methacrylate (DMAEMA) functionality show promise as microcapsule-forming pairs for the entrapment of mammalian cells. For example, such materials have been used to encapsulate erythrocytes. [Shao, W., Y. Xiaonan, and W. T. K. Stevenson, *Microcapsules through polymer complexation I: Complex coacervation of polymers containing a high charge density*. Biomaterials, 1991. 12: p. 374; Shao, W., et al., *Microcapsules through polymer complexation II: By complex coacervation of polymers containing a low charge density*. Biomaterials, 1991.12: p. 479.]

Early in vivo results with the alginate-polylysine system have not always been consistent because of the uncontrolled purity of alginate, and presumably also because of the incorporation of cells into the external membrane. The in vivo mechanical stability of microcapsules made by the new two-step technique remains to be tested, because the calcium ions are stripped. Even for microcapsules made by the standard technique, there is evidence that materials resembling alginate were around the microcapsules in the brain parenchyma of rats four weeks post-implantation. [Aebischer, P., et al., *Transplantation of polymer encapsulated neurotransmitter secreting cells: Effect of the encapsulating technique*. Transactions of the ASME, 1991. 113: p. 178.] Totally synthetic membranes can be more stable but they might not be the optimal substrates for cell growth and function.

Interfacial precipitation also has been used to form microencapsulates. In this method, cell suspension and polymer solution are extruded separately through two concentrically configured needles into a precipitating bath. Organic solvents such as dimethyl sulfoxide (DMSO), dimethyl formamide (DMF), dimethyl acetamide (DMAc), diethyl phthalate, and acetone are used to dissolve the organic polymers. Contact of cells with organic solvents is unavoidable but can be minimized through various coextrusion schemes.

Encapsulation of chromaffin and PC12 cells was achieved by this technique using poly(acrylonitrile-co vinyl chloride) as the membrane, in configurations of 1 cm long hollow fibers. [Aebisher, P., et al, *Transplantation of polymer encapsulated neurotransmitter secreting cells: Effect of the encapsulating technique.* Transactions of the ASME, 1991. 113: p. 178; Aebischer, P., et al., *Macroencapsulation of dopamine-secreting cells by coextrusion with an organic polymer solution.* Biomaterials, 1991. 12: p. 50.] In vitro and in vivo studies show that both cell viability and cell functions were largely preserved in the encapsulation process despite the fact that the cells were in contact with DMF or DMAc. No microcapsules have been prepared from this polymer-solvent system.

RL®, a water-insoluble polyacrylate available from Monsanto, has been used to form membrane for encapsulating erythrocytes and fibroblasts. [Boag, A. H. and M. V. Sefton, *Microencapsulation of human fibroblasts in a water-insoluble polyacrylate.* Biotech. Bioeng, 1987. 30: p. 854.] Diethyl phthalate was used as the organic solvent and a mixture of corn oil and mineral oil was used as the precipitating bath. Fibroblasts did not grow in the microcapsules unless collagen was also co-encapsulated and the microcapsules are fragile. [Broughton, R. L. and M. V. Sefton, *Effect of capsule permeability on growth of CHO cells in Eudragit RL microcapsules: use of FITC-dextran as a marker of capsule quality.* Biomaterial, 1989. 10: p. 462]

Subsequently, cationic polyacrylates involving the copolymers of MMA-DMAEMA were used to improve mechanical stability. [Mallabone, C. L., C. A. Crooks, and M. V. Sefton, *Microencapsulation of human diploid fibroblasts in cationic polyacrylates.* Biomaterials, 1989. 10: p. 380.] Growth of the encapsulated human diploid fibroblasts and Chinese hamster ovary (CHO) cells, however, was deemed unsatisfactory due to poor permeability for nutrients. [Broughton, R. L. and M. V. Sefton, *Effect of capsule permeability on growth of CHO cells in Eudragit RL microcapsules: use of FITC-dextran as a marker of capsule quality.* Biomaterials, 1989. 10: p. 462.]

Continued improvement led to macroporous MMA-hydroxyethyl methacrylate (MMA-HEMA) microcapsules that have higher permeability. [Crooks, C. A., et al., *Microencapsulation of mammalian cells in a HEMA-MMA copolymer: Effects on capsule morphology and permeability.* J. Biomed. Matr. Res., 1990. 24: p. 1241.] Evaluation of encapsulated hepatoma cells (HepG2) indicated that the cells formed aggregates instead of adhering to the copolymer, with central necrosis at day 7 in in vitro culture. [Babensee, J. E., U. D. Boni, and M. V. Sefton, *Morphological assessment of hepatoma cells (HepG2) microencapsulated in a HEMA-MMA copolymer with and without Matrigel.* J. Biomed. Matr. Res. 1992. 26: p. 1401.] Co-encapsulating Matrigel, a reconstituted extracellular matrix derived from mouse tumor basement membrane, did improve the cell viability.

A two-step process to encapsulate cells involving in situ polymerization has been reported. [Caidic, C., C. Baquey, and B. Dupuy, "Inverted Microcarriers" for cell cultures made by polymerization of shells around agarose microspheres in a non-cytotoxic procedure. Polymer, 1991. 23(8): p. 933] First the cells were encapsulated by extruding cell suspensions in agarose solution into 4° C. paraffin oil. A polymer shell composed of polyacrylamide was formed around each bead using a latex-seeded photoinduced polymerization process. Cell viability was demonstrated by continuous secretion of prolactin from encapsulated rat pituitary cells for three days; the cells were not yet responsive to alterations in potassium levels at this time point.

Whereas synthetic microcapsules are mechanically and chemically more stable than the polyelectrolyte gels composed of polysaccharides, low permeability is consistently an issue. These synthetic polymers are also not optimal substrates for cell attachment, growth and functions.

There remains a need for effective microencapsulation of living cells.

SUMMARY OF THE INVENTION

An object of the invention is to provide an effective encapsulation of living cells.

It is a further object of the invention to provide cell encapsulation which is characterized by good chemical and mechanical stability.

It is a still further object of this invention to provide an encapsulation for living cells which permits the cells to remain viable when introduced into a host.

It is another object of the invention to provide encapsulated living cells which remain viable when introduced into a host yet are protected against, inter alia, immunological rejection by the host.

It is yet another object of the invention to provide an encapsulation method which requires only mild encapsulation conditions.

In accordance with this invention there is provided living cells encapsulated in a membrane which is a complex formed by the cohesion of two polymer layers. An inner layer comprises a biopolymeric substrate polymer and an outer layer comprises a biocompatible synthetic polyelectrolyte having an electrolytic charge opposite that of the substrate polymer.

The membrane is formed by the cohesion of the oppositely-charged polymer layers to form a complex of substrate polymer and synthetic polyelectrolyte. The biopolymeric substrate polymer can support cell attachment where necessary, can maintain cell function, and has sufficient charge density to form a microencapsulating membrane by complex coacervation. The outer layer comprises a synthetic polyelectrolyte having an electrolytic charge opposite that of the substrate polymer. The synthetic electrolytic outer layer imparts stability and affords the opportunity to adjust transport properties.

Living cells encapsulated in the membrane remain viable and are protected within the membrane, which is permeable to nutrients, ions, oxygen, and other materials necessary to sustain the normal metabolic functions of the cell, as well as to products released by the cell, such as insulin released in response to glucose. However, the membrane is impermeable to bacteria, lymphocytes, large proteins, and other entities of the type responsible for immunological reactions that typically result in rejection of cells from the host's immune system.

DETAILED DESCRIPTION OF THE INVENTION

The selectively permeable, biocompatible membrane of this invention allows living cells to remain viable, yet protects the cells against, for example, immunological rejection by the host. It has been discovered that such a membrane can be formed by complex coacervation of two oppositely-charged polymeric layers if the polymers have sufficient charge density to cohere.

An inner layer of the membrane comprises a substrate biopolymer and an outer layer comprises a synthetic polyelectrolyte having an electrolytic charge opposite that of the substrate polymer. The substrate biopolymer has sufficient charge density to cohere to an oppositely-charged, synthetic polyelectrolyte to form a membrane at physiologic pH encapsulated cells, support cell attachment, if needed, and maintain cell function. The outer layer imparts stability and affords the opportunity to adjust transport properties.

Both naturally-occurring and modified biopolymers are suitable for use as biopolymers in the practice of the invention, as are both cationic and anionic biopolymers. The biopolymers will be water soluble and be characterized by a molecular weight of more than about 200,000.

Whereas collagen has been used to encapsulate drugs, it has not found widespread use for encapsulating cells because, at neutral pH, there is insufficient charge density to form an encapsulating membrane. It has been discovered that collagen modified to raise its pKI is sufficiently positively charged (a cationic polymer) at physiological pH to be complexed with oppositely-charged synthetic polyelectrolyte to form a cohesive membrane. Collagen can be modified to form a more strongly basic polymer by converting the primary amino groups to tertiary amine groups or by esterification.

In addition to collagen, cationic biopolymers useful in forming the polymeric membranes of the present invention include high molecular weight proteins such as fibrin, polylysine and the like. In general, the cationic biopolymer should have a pKI of at least about 9 and desirably at least about 10.

Anionic biopolymeric materials, such as hyaluronic acid (HA) and modified HA (esterified HA or amine modified HA) are useful in the invention. In general, anionic biopolymers suitable for the practice of this invention will have a charge density of at least about 50%. Modified HA, HA that is partially esterified or reacted with a primary amine to render it less water soluble, will form a stronger complex with the polycationic outer layer than HA itself.

Preferred biopolymers are modified HA, and modified collagen. Esterified collagen is particularly preferred as the inner layer. In general, the inner layer, though water-soluble, will be slightly hydrophobic.

Esterification or reaction to form tertiary amine groups on the biopolymer may be accomplished by reaction of the biopolymer with a wide variety of aliphatic reactants containing as many as about 18 carbon atoms in their chain. Such reactants will include inter alia, alcohols, primary amines and alcohol amines. Preferred reactants will contain about 8 carbon atoms or less. For some purposes, use of reactants having only 2 or 3 carbon atoms may be preferred. Typical alcohols will include methanol, ethanol, butanol and higher alcohols whereas typical primary amines will include methylamine, ethylamine and higher amines. Reactants with both alcohol and amine groups can also be used, such as ethanolamine. Reactants should be chosen so as to not impair the viability of the cells.

Suitable methods for obtaining the modified biopolymers having sufficient charge density to form a complex with synthetic materials to form a selectively permeable membrane, yet retaining the capability of maintaining cell function and differentiation are easily within the skill of the art.

The outer layer of the membrane comprises a biocompatible synthetic polyelectrolyte having a charge opposite that of the biopolymer. Thus, when the biopolymer is polycationic (for example, modified collagen), the synthetic polyelectrolyte used in the outer layer is polyanionic. A synthetic polycationic outer layer is used with HA, modified HA, and other polyanionic substrate polymers. Suitable outer layer synthetic polyelectrolytes form a complex with the oppositely-charged biopolymer to form a membrane by the complex coacervation process and impart stability to the encapsulate. In general, the charge density of the synthetic polymer will be at least about 3%. Like the biopolymers, the synthetic polyelectrolyte will generally have a molecular weight of at least about 200,000.

Biocompatible synthetic polyelectrolytes are known in the art and generally can be used in the practice of this invention. A preferred class of biocompatible synthetic polyelectrolytes are acrylate polymers. Such polymers include acrylate polymers, copolymers and terpolymers such as poly(acrylic acid), poly(methacrylic acid) poly(methacrylate), poly(methyl methacrylate) and acrylate copolymers and terpolymers of acrylic acid, methacrylic acid, methacrylates, methyl methacrylates, hydroxyethyl methacrylic such as 2-hydroxyethyl methacrylate, hydroxypropylacrylate and the like, and blends thereof. Poly(dimethylaminoethyl methacrylate) ("DMAEMA") and copolymers and terpolymers of dimethylaminoethyl methacrylate with 2-hydroxyethyl methacrylate and/or hydroxypropylacrylate and methacrylate and/or methyl methacrylate are preferred cationic synthetic polymers. Copolymers or terpolymers of acrylic acid and/or methacrylic acid with 2-hydroxyethyl methacrylic and/or hydroxypropylacrylate and methacrylate and/or methyl methacrylate are preferred anionic synthetic polymers. Each has exhibited biocompatibility when used in other biomaterials.

The membrane of the encapsulated cell is selectively permeable. The cells encapsulated in accordance with the invention remain viable because the membrane is permeable to nutrients and other materials necessary to support the normal metabolic functions of the cells. Thus, ionic materials and oxygen, for example, pass through the membrane. The membrane also is permeable to products of the cells, such as hormones, and to metabolic byproducts. Thus, material produced by the cell can pass through the membrane from the interior of the capsule. In this way, material produced by the encapsulated cell can be introduced into the blood of a host, or can be introduced into a culture medium in which encapsulated cells are placed.

The membrane permeability is such as to essentially preclude entry of bacteria, lymphocytes, large proteins, and other entities of the type responsible for immunological reactions that typically result in rejection of the cells from the host's immune system.

The composition of the outer layer can be modified to adjust the permeability and transport properties of the membrane. As an example, the permeability of the membrane to typically polar compounds found in biological systems can be increased by incorporating a hydrophilic copolymer, such as poly(2-hydroxyethyl methacrylate) (HEMA) or other hydroxy-containing acrylates, into the polyelectrolyte comprising the outer layer of the membrane. The more hydrophobic polyelectrolytes tend to be less permeable.

The permeability of the membrane also can be adjusted by selection of molecular weight or structure of the outer layer so as to preclude molecules having a preselected molecular weight or structure from passing through the membrane. As the molecular weight of the polyelectrolytic is increased the membrane tends to be more permeable. Larger differences in charge densities between the inner biopolymer and the outer polyelectrolyte also tend to make the membrane more permeable. The mechanical stability of the membrane can be improved by increasing the molecular weight of the polyelectrolyte in the outer layer or by choice of monomers for the polyelectrolyte. The nature of the modification to the inner biopolymer (e.g.; length of alcohol or amine) can have a minor effect on permeability (the longer chains tend to lower permeability, the major component affecting permeability in the outer layer).

The membrane is formed by complex coacervation by combining drops of a solution of biopolymer with a solution of synthetic polymer at physiological or neutral pHs of from about 6 to about 8 so as to avoid adversely affecting the viability of the cells. In such process, the biopolymer is dissolved in a suitable aqueous solvent that will not adversely affect the viable cells. Such solvents are well known and include buffered saline, culture medium and the like. Similarly the synthetic polyelectrolyte is soluble in and dissolved in a suitable solvent that will not threaten the viability of the cells. Such solvents include aqueous solvents such as buffered saline, culture medium and the like. The solvent used for the biopolymer does not need to be the same solvent used for the synthetic polymer. Mild agitation of the polyelectrolytic solution can be utilized if desired.

In one suitable technique, a substrate polymer solution containing a cell suspension in a suitable diluent such as phosphate buffered saline (PBS) is added dropwise to a receiving solution containing synthetic polyelectrolyte of the opposite charge in PBS at ambient temperature. A cohesive membrane is formed at the interface of the two solutions to provide encapsulated cells. Advantageously, no organic solvent is required and no crosslinking reaction is necessary. Thus, the conditions of encapsulation are especially mild, yielding little cell mortality.

The proper matching of biopolymer and synthetic polyelectrolyte can readily be confirmed. It is only necessary to add a drop of a solution of biopolymer to a solution of electrolyte. Proper matching results in the rapid formation of a capsule. The suitability of a given encapsulate regarding permeability can readily be determining by in vitro tests using standard cell culture media.

The concentrations of the polymer solutions, the size of the droplets added to the synthetic polyelectrolyte solution, and the rate at which the substrate polymer solution containing cell suspension is added to the synthetic polyelectrolyte solution can be adjusted to achieve an encapsulating membrane having the desired thickness of layers and desired size. Suitable concentrations for the biopolymer solution and for the synthetic polyelectrolyte solution will vary depending upon the specific polymers and solvents employed but is easily within the skill of the art. While it is not possible to delineate concentrations for all possibilities, the concentration of the biopolymer often will be from about 0.1 to about 2% whereas the concentration of the synthetic polyelectrolyte will be from about 2 to about 6%.

The thickness of the inner, substrate polymer layer, will depend, inter alia, on the viscosity of the biopolymer solution and the degree of penetration into the synthetic polyelectrolyte solution achieved by the substrate polymer solution droplets. The degree of penetration is related to the molecular weight of the polyions and the viscosity of the solutions.

The practice of this invention provides microspheres which may range in size from as small as about 30 microns to as large as several millimeters. The larger sizes are most suitable for cells which tend to aggregate such as islet of Langerhans cells and the like.

The number of cells within each capsule can be readily controlled and is a function of the density of the cell suspension within the biopolymer. For example, cells in PBS (which may be at densities of $10^3$ to $10^6$ cells per ml) can be mixed with the biopolymer to provide a variety of cell concentrations. Individual capsules can contain any desired number of cells ranging from only one to 20 cells, to 50 or 100 cells or more.

Because the membrane of the encapsulated cells of the invention precludes contact between the cells and the host's immune mediators, all types of living cells, including both naturally-occurring and genetically-engineered cells, may be encapsulated. The encapsulates are suitable for anchorage independent cells and are particularly suitable for encapsulation of anchorage-dependent living cells.

Encapsulated cells of the invention are useful as, for example, a hormone-producing system. Use of cells microencapsulated in a selectively-permeable biopolymeric membrane affords the opportunity to provide artificial organs and other methods for improving and restoring functions in people with physical disabilities.

An example of one type of hormone-producing cell is a cell of the anterior pituitary gland. Such cell excretes growth hormone which, inter alia, stimulates skeletal growth. In accordance with the invention, encapsulated naturally-occurring anterior pituitary cells are therefore useful in stimulating skeletal growth in a host. The encapsulated cells provide growth hormone produced by the cells and introduced to the blood of a host through the encapsulating membrane. Growth hormone also can be produced by genetically-engineered microorganisms. Such microorganisms, when encapsulated, may be used to provide growth hormone to a host.

Encapsulated cells which secrete hormones also may be suspended in a culture medium and will excrete hormone over an extended period. Encapsulated insulin-producing cells, for example, mammalian pancreatic alpha cells, beta cells, or intact islets of Langerhans, may also be used as an artificial pancreas. Such encapsulated cells can be implanted into a diabetic mammal and will function in vivo to excrete insulin and other hormones in response to host blood glucose concentration. Similarly, encapsulated hepatocytes may be used as an artificial liver, such as for a patient experiencing fulminant hepatic failure.

Other types of cells also may be beneficially encapsulated. For example, encapsulated neurotransmitter-secreting cells may be used to treat neurological disorders such as Parkinson's and Alzheimer's diseases. Similarly, chromaffin cell transplants may be used for alleviation of pain, especially chronic pain, and encapsulated chondrocytes may be used for repair of musculoskeletal defects.

Skilled practitioners recognize the utility of encapsulating living cells, and will be able to identify still further cells suitable for encapsulation in accordance with the invention.

Even though the membrane may be permeable to proteases that can digest collagen and other biopolymers used to form the inner layer of the membrane, applicant has found that the inner layer remains intact. Without being bound by any theory, it is believed that the proteases cannot digest the modified collagen, HA, modified HA, or other biopolymer when the biopolymer is complexed with the outer layer. This resistance can be analogized to the resistance to solubilization of type I collagen and to cross-linked collagen, such as is found in heart valve tissue. Again, without wishing to be bound by theory, it is postulated that the complexation shields or changes the conformation of the cleavage site (between glycine and leucine), thus making the resulting complexed biopolymer resistant to degradation.

The length of the period during which encapsulated cells remain intact will depend upon the properties of the medium in which the encapsulated cells are used and upon the composition of the biopolymer and of the synthetic polyelectrolyte. For example, encapsulated cells used in a culture medium might be expected to remain intact for a longer period than encapsulated cells introduced into a human or animal body. Also, the mechanical stability of the membrane can be improved by increasing the molecular weight of the synthetic polyelectrolyte. Skilled practitioners will be able to determine the length of the period during which encapsulated cells remain intact in various media.

The following example should not be construed so as to limit the claims in any way. Rather, the example merely illustrates the invention, and in particular, shows that cells encapsulated in a membrane having an esterified collagen inner layer and a methacrylic acid/HEMA/methyl methacrylate ter-polymer outer layer remained viable for at least up to four days. The example also shows that bovine serum albumin (MW=67,000) was completely released in 15 minutes when encapsulated in the same membrane, whereas less than 10 percent of alcohol dehydrogenase (MW=1,500,000) was released from such a membrane in one hour.

EXAMPLE

Collagen was esterified by reacting with methanol for three days in the presence of 0.1M HCl. Terpolymer of methacrylic acid, 2-hydroxyethyl methacrylate and methyl methacrylate was polymerized in accordance with known techniques with 1,1'-azobis(cyclohexane carbonitrile) as the initiator. The polyelectrolytes were characterized by NMR and potentiometric titration.

Microcapsules were formed by extruding a 0.5% solution of modified collagen in phosphate buffered saline (PBS) solution through a polyethylene tubing using a syringe pump into a 3% solution of synthetic polymer in PBS. To observe the structure of the microcapsules, collagen was labelled with Texas red and the synthetic polymer with FITC for confocal microscopy. The morphology of the microcapsules was observed by scanning electron microscopy.

NIH mouse 3T3 fibroblasts were encapsulated at an initial density of $2 \times 10^4$ cells/ml and incubated in DMEM containing 10 percent calf serum and 8–10 percent $CO_2$ at 37° C. Cell viability and growth inside the microcapsules were assessed by uptake of fluorescein diacetate, and cell death was visualized by uptake of propidium iodide. Bovine serum albumin (BSA) and alcohol dehydrogenase were encapsulated in separate experiments for diffusion studies.

The esterified collagen exhibited simple base characteristics as analyzed by potentiometric titration. This allowed the formation of stable microcapsules at physiological pH when it was complexed with a strong synthetic polyanion. The confocal microscopic analysis shows that the internal layer of the microcapsules was predominantly composed of collagen. The diffusion experiments showed that BSA (MW=67,000) was completely released in 15 minutes, while less than 10 percent of alcohol dehydrogenase (MW=1,500,000) was released in an hour.

Fibroblasts were first cultured on culture dishes coated with modified collagen and the synthetic polymer to test their suitability as substrates. No statistically significant differences in terms of growth rate and morphology were observed compared to collagen and TCPS as controls. Cells encapsulated in microcapsules were viable as observed by their uptake of fluorescein diacetate just after encapsulation and 48 hours after encapsulation. The fluorescence analysis also showed clearly growth and spreading of the fibroblasts. At 48 hours post-encapsulation, uptake of propidium iodide was almost non-detectable. The microcapsules encapsulated with fibroblasts were observed to contract up to 50 percent of their original size at 4 days post-encapsulation. In contrast, blank microcapsules shrank by only 20 percent. It is known that fibroblasts cultured in three dimensional collagen shrink the gel by as much as 60 percent. The contraction data indicated that the encapsulated cells are functional four days after encapsulation.

We claim:

1. A biocompatible microcapsule suitable for introduction into a host, said microcapsule comprising:
   (a) bioactive cells enclosed within a membrane,
   (b) said membrane comprising an inner layer and an outer layer, said inner layer comprising a cationic biopolymer consisting of collagen modified to have a pKI of at least about 9 or an anionic biopolymer selected from the group consisting of esterified hyaluronic acid and amine modified hyaluronic the cells and supporting acid and said inner layer containing the cells and supporting maintenance of cell function, said outer layer comprising a biocompatible synthetic polyelectrolyte having an electrolytic charge opposite to that of the inner layer, said inner and outer layer having charges sufficient to form a complex of said biopolymer and said polyelectrolyte when a solution of the biopolymer containing a suspension of the bioactive cells is introduced into a solution of the synthetic polyelectrolyte,
   (c) said membrane being permeable to materials necessary to sustain the normal metabolic functions of the bioactive cells and to products released by the bioactive cells and impermeable to immune system components responsible for immunological reactions that result in immune rejection of the bioactive cells by the host.

2. The biocompatible microcapsule of claim 1, wherein the bioactive cells are attachment-dependent.

3. The biocompatible microcapsule of claim 1, wherein the bioactive cells are attachment-independent.

4. The biocompatible microcapsule of claim 1, wherein the synthetic polyelectrolyte is an acrylate copolymer or terpolymer containing (a) at least one of acrylic acid and methacrylic acid and (b) at least one of hydroxyethyl methacrylate and hydroxylproply methacrylate.

5. The biocompatible microcapsule of claim 1 wherein the bioactive cells are selected from the group consisting of intact islets of Langerhans, alpha cells, beta cells, and mixture thereof, and the product released by the bioactive cells is insulin.

* * * * *

UNITED STATES PATENT AND TRADEMARK OFFICE
CERTIFICATE OF CORRECTION

PATENT NO. : 5,620,883
DATED : September 1, 1999
INVENTOR(S) : Wen SHAO et al.

It is certified that error appears in the above-identified patent and that said Letters Patent is hereby corrected as shown below:

In claim 1 at column 12, line 30, delete "the cells and supporting".

Signed and Sealed this

Twenty-sixth Day of September, 2000

Q. TODD DICKINSON

Attest:

Attesting Officer

Director of Patents and Trademarks